(12) United States Patent
Mimoun

(10) Patent No.: US 6,770,588 B2
(45) Date of Patent: Aug. 3, 2004

(54) REDUCTION OF CARBONYL COMPOUNDS BY A SILANE IN THE PRESENCE OF A ZINC CATALYST

(75) Inventor: Hubert Mimoun, Challex (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/345,285

(22) Filed: Jan. 16, 2003

(65) Prior Publication Data

US 2003/0171210 A1 Sep. 11, 2003

Related U.S. Application Data

(62) Division of application No. 09/836,682, filed on Apr. 6, 2001, now Pat. No. 6,533,960, which is a division of application No. 09/259,880, filed on Mar. 1, 1999, now Pat. No. 6,245,952.

(30) Foreign Application Priority Data

Apr. 1, 1998 (CH) ............................................. 0778/98

(51) Int. Cl.[7] .......................... B01J 31/00; C07F 3/06; C07F 3/08; C07F 3/10
(52) U.S. Cl. ...................... 502/167; 502/171; 502/172; 556/118; 556/119; 556/120; 556/121; 556/122; 556/123; 556/124; 556/125; 556/126; 556/127; 556/128; 556/129; 556/130; 556/131; 556/132; 556/133; 556/134; 556/135
(58) Field of Search ................................. 502/167, 171, 502/172; 556/118–135, 564

(56) References Cited

U.S. PATENT DOCUMENTS

| | | | | |
|---|---|---|---|---|
| 3,061,424 A | | 10/1962 | Nitzsche et al. ............... 75/108 |
| 5,126,305 A | * | 6/1992 | Eling .......................... 502/167 |
| 5,220,020 A | | 6/1993 | Buchwald et al. ........... 544/106 |
| 5,227,538 A | | 7/1993 | Buchwald et al. ........... 568/814 |
| 5,449,736 A | | 9/1995 | Cabasso et al. ............... 528/25 |
| 5,831,133 A | | 11/1998 | Mimoun ...................... 568/814 |
| 6,046,127 A | * | 4/2000 | Mimoun ...................... 502/170 |
| 6,245,952 B1 | * | 6/2001 | Mimoun ...................... 568/814 |
| 6,392,103 B1 | * | 5/2002 | Mimoun ...................... 568/814 |
| 6,533,960 B2 | * | 3/2003 | Mimoun .................... 252/188.1 |
| 6,573,395 B2 | * | 6/2003 | Mimoun ...................... 556/127 |

FOREIGN PATENT DOCUMENTS

WO    WO 96/12694    3/1996

OTHER PUBLICATIONS

Barr et al., "Titanocene–Catalyzed Reduction of Esters Using Polymethylhydrosiloxane as the Stoichiometric Reductant," *J. Org. Chem.*, vol. 59, No. 15, 4323–4326 (1994).
Breeden et al., "Reduction of Carboxylic Esters and Acids by Polymethylhydrosiloxane catalysed by Titanium and Zirconium alkoxides," *Synlett*, 833–835 (1994).
Chandrasekhar et al., "Chemoselective Reduction of Carbonyl Compounds with PMHS—$ZnCl_2$," *Synthetic Communications*, 27(13), 2251–2254 (1997).
Kobayashi, *Tetrahedron*, vol. 53, No. 5, 1627–1634 (1997).
Lawrence, *J. Chem. Soc., Perkin Trans.1*, 3381–3391 (1999).
Nietzsche et al., "Reduktionen mit Methyl–wasserstoff–polysiloxanen," *Agnew. Chem.*, vol. 69, No. 3 (1957) XP–002083958.
Reding et al., "An Inexpensive Air–Stable Titanium–Based System for the Conversion of Esters to Primary Alcohols," *J. Org. Chem.*, vol. 60, No. 24, 7884–7890 (1995).
Singh et al., "Synthesis, Reactivity, and Catalytic Behavior of Iron/Zinc–Containing Species Involved in Oxidation of Hydrocarbons under Gif–Type Conditions," *J. Am. Chem. Soc.*, vol. 119, 7030–7047 (1997).
Verdaguer et al., "Catalytic Method for the Reduction of Lactones to Lactols," *J. Am. Chem. Soc.*, vol. 117, No. 50, 12641–12642 (1995).

\* cited by examiner

*Primary Examiner*—Mark L. Bell
*Assistant Examiner*—Jennine M. Brown
(74) *Attorney, Agent, or Firm*—Winston & Strawn LLP

(57) ABSTRACT

A reductive system including a silane, preferably PMHS, and an active zinc compound, which is monomeric and not a hydride, wherein a reduction of a carbonyl substrate to a corresponding alcohol is achievable.

7 Claims, No Drawings

REDUCTION OF CARBONYL COMPOUNDS BY A SILANE IN THE PRESENCE OF A ZINC CATALYST

CROSS REFERENCE TO RELATED APPLICATIONS

This application is a division of copending application Ser. No. 09/836,682 filed Apr. 6, 2001, now U.S. Pat. No. 6,533,960 which is a division of application Ser. No. 09/259,880 filed Mar. 1, 1999, now U.S. Pat. No. 6,245,952, the content of each of which is expressly incorporated herein by reference thereto.

BRIEF SUMMARY OF THE INVENTION

The present invention concerns the field of organic synthesis. It concerns, more particularly, a process for the selective reduction of carbonyl compounds, such as aldehydes, ketones, esters and lactones into the corresponding alcohols, using silanes as reducing agents, preferably polymethylhydrosiloxane (PMHS), in the presence of catalysts which comprise monomeric zinc compounds, complexed by basic ligands such as amines, polyamines, aminoalcohols, amine oxydes, amides, phosphoramides, etc.

BACKGROUND OF THE INVENTION

The selective reduction of carbonyl compounds to the corresponding alcohols in the course of which only the reaction of the C=O function is observed, is an important task in the field of organic chemistry. Until now, there were exclusively used hydride reducing agents, such as lithium aluminum hydride $LiAlH_4$, sodium borohydride $NaBH_4$, or sodium dihydroxybis(2-methoxyethoxy)aluminate (SDMA) of formula $NaAlH_2(OCH_2CH_2OCH_3)_2$, the two latter reagents being of limited value for the reduction of esters and lactones. All the above-mentioned reagents are employed in stoichiometric amounts and show the disadvantage of releasing hydrogen in the course of the reaction or, when entering into contact with humidity, of leading to explosion risks and requiring the inertization of the reactors used. Furthermore, the use of these reagents is costly as they are required in stoichiometric amounts. Thus, there is a continuous search for other systems which are more economic and easier to use.

Several publications describe the use of silanes as reducing agents for carbonyl substrates, together with a metal catalyst. A preferred silane for this type of reductions is polymethylhydrosiloxane or PMHS, according to the general formula

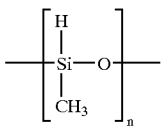

U.S. Pat. No. 3,061,424 to Nitzsche and Wick describes the reduction of aldehydes and ketones with PMHS and a salt of mercury, iron, copper, titanium, nickel, zirconium, aluminum, zinc, lead, cadmium and, as the preferred embodiment, tin. This reductive system requires activation by a proton source, without which the reaction does not proceed. However, the system is not effective for the reduction of esters and lactones.

U.S. Pat. No. 5,220,020 to Buchwald et al. describes a method for the preparation of alcohols by the reduction of carbonyl compounds using a system composed of a silane reducing agent and a metal catalyst of formula $M(L)(L')(L'')$ to $M(L)(L')(L'')(L''')(L^{IV})(L^{V})$, in which M is a metal belonging to any of groups 3, 4, 5, or 6 of the periodical table, a lanthanide or an actinide, whereas ($L'$) to ($L^{V}$) represent hydrogen, an alkyl group, an aryl group, a silyl group, a halogen atom, or a —OR, —SR or —NR(R') group, R and R' being hydrogen, an alkyl or an aryl group. Amongst the preferred catalysts, the cited patent mentions titane (IV) isopropylate or ethylate or trichlorotitane (IV) isopropylate. Such a system is said to be appropriate for the reduction of esters, lactones, amides or imines. More recently, Breedon and Lawrence (Synlett., 1994, 833) and Reding and Buchwald (J. Org. Chem., 1995, 60, 7884) have described a similar process, namely the use of non-activated titane tetraalkoxydes as catalysts for the reduction of esters by PMHS. The method described in those three mentioned references requires the use of large amounts, at least 25 mole % with respect to the substrate, of catalyst. Barr, Berk and Buchwald (J. Org. Chem., 1994, 59, 4323) have shown that the complex $Cp_2TiCl_2$, when reduced by butyllithium or ethylmagnesium bromide, could catalyze the reduction of esters into the corresponding alcohols with good yields, but this technique requires reagents which are expensive and difficult to use in a large scale, as is the case in industrial organic synthesis.

As closest prior art, there should be cited the international application WO 96/12694 of the applicant, describing the reduction of aldehydes, ketones, esters and lactones by a reductive system composed of silanes and a metal hydride, leading to the corresponding alcohols with good yields. This systems requires only very low amounts of catalyst, i.e. the metal hydride, in the order of 1 mol % with respect to the substrate. The hydride is formed by the reaction of a salt of the respective metal with an appropriate reducing agent, preferably $NaBH_4$. Besides zinc salts, cobalt, manganese and iron salts are used as precursors for the generation of metal hydrides. According to another preferred embodiment, PMHS is used as silane reducing agent.

DETAILED DESCRIPTION OF THE INVENTION

We have now successfully developed a process for the reduction of carbonyl compounds with silanes, catalyzed by metal derivatives which are not hydrides and which, in consequence, do not require the use of a reducing agent like, for example, $NaBH_4$.

The object of the invention is a process for the preparation of alcohols by reduction of the carbonyl function in substrates belonging to the class of aldehydes, ketones, esters or lactones, which substrates may contain unsaturated functions other than the carbonyl group, wherein a) said carbonyl substrate is reacted with an effective amount of a silane, preferably PMHS, in the presence of catalytic amounts of an active zinc compound which is monomeric and not a hydride, to form a siloxane, b) the thus-obtained siloxane is hydrolyzed with a basic agent to form an alcohol, and c) the resulting alcohol is separated and purified, if necessary.

Another object of the invention is a reductive system comprising a) a silane, preferably PMHS, and b) an active zinc compound which is monomeric and not a hydride.

The present invention is based on the surprising fact that the use of a monomeric species of zinc considerably enhances the reactivity of a reductive system for carbonyl compounds comprising a silane and a zinc compound. Thus, reductive systems comprising a zinc salt and a silane, as described in U.S patent U.S. Pat. No. 3,061,424 to Nitzsche and Wick which has been cited beforehand, are by far less reactive than the system according to the present application. In particular, the system as described in the prior art is not capable of reducing esters and lactones, in contrast to the reductive system of the present invention.

On the other hand, although the above-cited document WO 96/12694 of the applicant shows that it is possible to enhance the reactivity of a silane for the reduction of carbonyl substrates by adding zinc salts or complexes, the latter require the activation by a reducing agent. As reducing agent, compounds like $NaBH_4$, $LiAlH_4$, lithium or aluminum alkyls or Grignard compounds were used to generate a highly reactive species, namely a hydride.

The present invention, however, uses zinc compounds such as salts or complexes which do not require the activation by a reducing agent and which, when employed in stoichiometric amounts and together with a silane, catalyze the reduction of all sorts of carbonyl compounds.

The chemistry of zinc is in general characterized by the tendency of the metal to reach a coordination number higher than 2 which is a consequence of its valence state +2. The zinc can reach the higher coordination number it desires to attain by oligo- or polymerization, after which in general a tetra- or hexacoordination is observed. For those reasons, zinc salts or complexes are in most cases oligo- or polymeric, and as examples, there are mentioned here zinc carboxylates and halides.

However, an electronically unsaturated class of compounds are dialkyl- and diaryl zinc compounds. They are not capable of reaching a higher coordination number than 2 by oligo- or polymerization because alkyl and aryl groups cannot act as bridging ligands. Dialkyl- and diaryl zinc compounds are therefore monomeric, and they show a linear structure.

We have established that all the above-mentioned compounds show either no activity or a very low activity when used for the reduction of carbonyl compounds. However, these poly- or oligomeric species as well as dialkyl- or diaryl zinc compounds, when treated with an appropriate complexing agent which is capable of generating a monomeric active species, become highly effective catalysts for the reduction of aldehydes, ketones, esters and lactones by a silane.

According to the invention, there can be used an oligo- or polymeric precursor compound or a dialkyl- or diaryl zinc compound, which is converted into an active salt or complex by treatment with an appropriate complexing agent. Moreover, we have found that there can also be used known monomeric complexes or salts which turned out to be active in the process of the invention, but whose activity has passed completely unnoticed until now.

As the precursor compound, practically any known compound of zinc according to the general formula $ZnX_2$ can be used. In this formula, X stands for any anion. Preferred anions X are defined below.

The active catalyst of the invention can be described by the general formula $ZnX_2L_n$. The catalyst can be obtained in situ, in the reaction medium, or be prepared separately from a zinc compound such as, for example, a salt or complex of general formula $ZnX_2$, mentioned above. In the formula $ZnX_2$ of the precursor compound and $ZnX_2L_n$ of the active catalyst, X is preferably any anion selected from the group consisting of carboxylates, β-diketonates, enolates, amides, silylamides, halides, carbonates and cyanides and organic groups such as alkyl, cycloalkyl, alkoxy, aryl, aryloxy, alkoxyalkyl, alkoxyaryl, aralkoxy, aralcoyl and alkylaryl groups. Amongst this group, one will preferably use a zinc carboxylate of formula $Zn(RCO_2)_2$ like, for example, the acetate, propionate, butyrate, isobutyrate, isovalerate, diethylacetate, benzoate, 2-ethylhexanoate, stearate or naphthenate; a zinc alkoxyde of formula $Zn(OR)_2$, wherein R is an alkyl group from $C_1$ to $C_{20}$, preferably from $C_1$ to $C_5$ such as, for example, the methoxyde, ethoxyde, isopropoxyde, tert-butoxyde, tert-pentoxyde, or the 8-hydroxyquinolinate; a zinc β-diketonate like, for example, the acetylacetonate, substituted or unsubstituted, or the tropolonate; a compound of the type alkylzinc, arylzinc, alkyl(alkoxy)zinc or aryl(alkoxy)zinc comprising from 1 to 20 carbon atoms, preferably from 1 to 5 carbon atoms or a derivative thereof such as, for example, dimethylzinc, diethylzinc, dipropylzinc, dibutylzinc, diphenylzinc, methyl(methoxy)zinc or methyl(phenoxy)zinc, or a derivative of the type halide(alkyl)zinc.

In the formula $ZnX_2L_n$, n is an integer from 1 to 6. The ligands L can be identical or different and be selected from the group consisting of amines, polyamines, imines, polyimines, aminoalcools, amines oxydes, phosphoramides and amides.

The amine may be a primary, secondary, or tertiary aliphatic, alicyclic or aromatic amine comprising from 2 to 30 carbon atoms. Non-limiting examples include aniline, triethylamine, tributylamine, N,N-dimethylaniline, morpholine, piperidine, pyridine, picolines, lutidines, 4-tertiobutylpyridine, dimethylaminopyridine, quinoline and N-methylmorpholine.

The polyamines may comprise from 2 to 6 primary, secondary or tertiary amine groups, and from 2 to 30 carbon atoms such as, for example, ethylenediamine, 1,2- and 1,3-propylenediamine, 1,2-, 1,3- and 1,4-butanediamine, hexamethylenediamine, N,N-dimethylethylenediamine, diethylenetriamine, dipropylenetriamine, triethylenetetramine, tetramethylethylenediamine, N,N-dimethylpropylenediamine, N,N,N'-trimethylethylenediamine, N,N,N',N'-tetramethyl-1,3-propanediamine, hexamethylenetetramine, diazabicyclononane, sparteine, orthophenantroline, 2,2'-bipyridine and neocuproine.

The aminoalcohols may comprise one or several primary, secondary or tertiary amine functions together with one or several primary, secondary or tertiary alcohol functions like in, for example, ethanolamine, diethanolamine, triethanolamine, dimethylaminoethanol, diethylaminoethanol, dimethylaminomethanol, diethylaminomethanol, 2-aminobutanol, ephedrine, prolinol, valinol, cinchonidine, quinine and quinidine.

As ligands belonging to the family of imines or diimines and capable of activating zinc derivatives or compounds in the context of the present invention, one can cite, as non-limiting examples, the compound families according to formulae [I] to [V] below, in which the groups $R_1$ to $R_6$ each represent a hydrogen atom or an alkyl, cycloalkyl, alkoxy, aryl, aryloxy, alkoxyalkyl, alkoxyaryl, aralkoxy, aralcoyl, alkylaryl or aralkyl goup comprising from 1 to 20 carbon atoms.

[I]

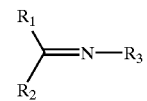

-continued

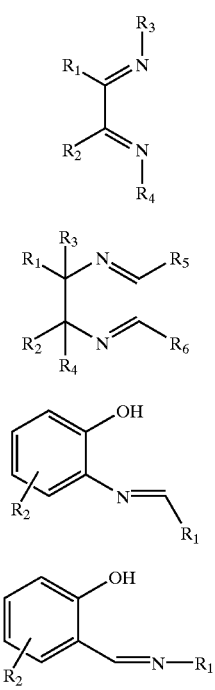

Other ligands capable of activating zinc compounds and derivatives yet include amides like, for example, dimethylformamide, dimethylacetamide or N-methyl-pyrrolidone, phosphoramides such as, for example, hexamethylphosphortriamide, phosphine oxides like, for example, triphenylphosphine oxide, tributyl- or trioctylphosphine oxide, amine oxides like, for example, pyridine N-oxyde, 4-picoline-N-oxyde, N-methyl-morpholine N-oxyde and sulfoxydes like, for example, dimethyl- or diphenylsulfoxyde.

The invention also concerns monomeric zinc complexes which turned out to be active in the process of the invention. A preferred class of compounds are monomeric zinc carboxylates. This class of molecules is not described in the chemical literature, with the exception of the compound $Zn(O_2CCH_3)_2(pyridine)_2$, see J. Am. Chem. Soc. 119, 7030, (1997).

As preferred compounds amongst these complexes, there are cited here $[Zn(benzoate)_2(Me_2NCH_2CH_2OH)_2]$, $[Zn(diethylacetate)_2(2,2'-bipyridyl)]$, $[Zn(diethylacetate)_2(1,2-diaminopropane)_2]$ and $[Zn(benzoate)_2(TMEDA)]$ (TMEDA=tetramethylethylenediamine). The preparation and characterization of these compounds is described below.

A great number of silanes can be used in the process according to the present invention. Such silanes are known to a person skilled in the art, and they will be chosen according to their capacity to effectively reduce carbonyl substrates in the process according to the present invention. As non-limiting examples, there can be cited trialkylsilanes, dialkylsilanes or trialkoxysilanes. More specific examples include dimethylsilane, diethylsilane, trimethoxysilane and triethoxysilane. There will preferably be used PMHS due to its effectiveness, availability and price.

The process according to the present invention is lined out in the following reaction schemes, which apply to the particular and preferred case of employing PMHS as reducing agent.

Reduction of aldehydes ($R_1$=alkyl, aryl; $R_2$=H) and ketones ($R_1$, $R_2$=alkyl, aryl)

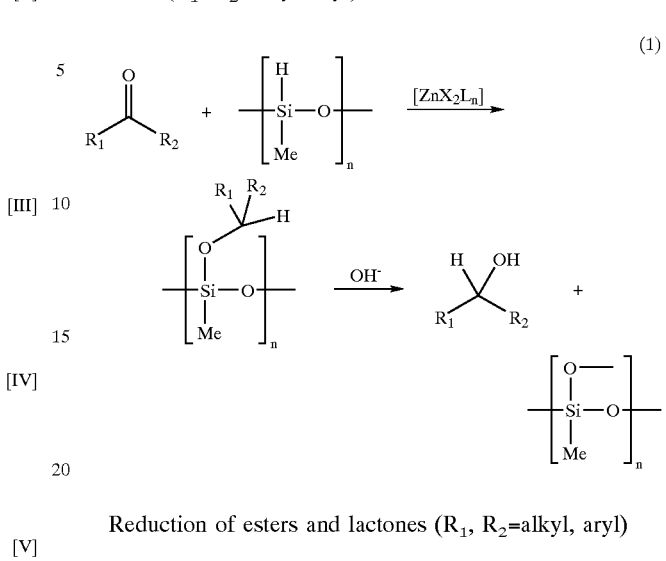

Reduction of esters and lactones ($R_1$, $R_2$=alkyl, aryl)

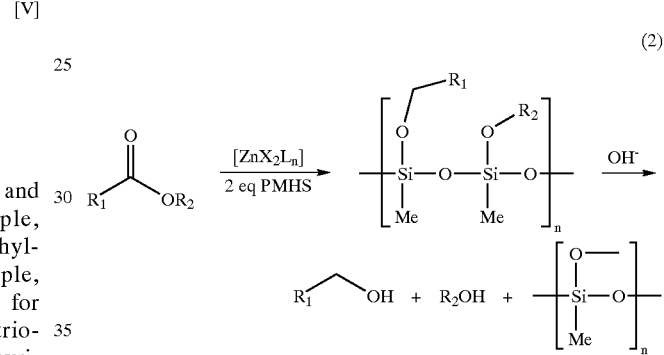

The concentration of the catalyst $ZnX_2L_n$, given in mole % with respect to the substrate, is generally from 0.1 to 10%, preferably from 1 to 5%.

There will typically be consumed 2 mole equivalents of PMHS per ester or lactone function, and one equivalent for the reduction of aldehydes and ketones. For practical reasons, there will preferably be used a slight excess of PMHS with respect to these stoichiometric amounts, in general of the order of 10 to 40% excess, based on the stoichiometric quantity. The reduction reaction according to the invention also takes place when the silane is used in sub-stoichiometric amounts, but this results in a decrease in conversion. According to the invention, therefore, the term "effective amount" means an amount of silane sufficient to induce reduction of the substrate.

The alcohol which is obtained as reaction product can be obtained by hydrolysis of the formed polysilylether. This hydrolysis may be carried out by adding to the reaction mixture an aqueous or alcoholic solution of a basic agent such as, for example, sodium or potassium hydroxide, lime or sodium or potassium carbonate. The ratio of the base with respect to the PMHS used will be from about 1 to 2 mole equivalents. After complete hydrolysis, there will in general be observed the formation of two phases. The desired alcohol is found in the organic phase and can be obtained by evaporation of the solvent which may be present. The obtained residue may be distilled for further purification.

The reduction can be carried without a solvent or in a solvent such as, for example, an ether (e.g. methyltertbutylether, diisopropylether, dibutylether, tert-amylmethylether, tetrahydrofurane or dioxane), an aliphatic hydrocarbon (e.g. heptane, petroleum ether, octane, or cyclohexane) or an aromatic hydrocarbon (e.g. benzene, toluene, xylene or mesitylene), or mixture thereof.

As laid out above, the reduction according to the invention is applicable to various carbonyl compounds which may contain unsaturated functionalities other than the carbonyl group such as, for example, olefin, acetylene, nitrile or nitro groups which will not be affected by the reduction reaction.

As non-limiting examples for aldehyde substrates, there can be cited butanal, pentanal, heptanal, octanal, decanal, dodecanal, linear or branched. Other aldehydes which are unsaturated and which can be selectively reduced into the corresponding unsaturated alcohols include acroleine, methacroleine, prenal, citral, retinal, campholene aldehyde, cinnamic aldehyde, hexylcinnamic aldehyde, formylpinane and nopal. Aromatic aldehydes like, for example, benzaldehyde, cuminic aldehyde, vanilline, salicylaldehyde or heliotropine are also easily reduced to the corresponding alcohols.

As non-limiting examples for saturated and unsaturated ketones which can be reduced into the corresponding alcohols by silanes according to the invention, there can be cited hexan-2-one, octan-2-one, nonan-4-one, dodecan-2-one, methylvinylketone, mesityl oxide, acetophenone, cyclopentanone, cyclododecanone, cyclohexen-1-en-3-one, isophorone, oxophorone, carvone, camphor, beta-ionone, geranylacetone and 2-pentylcyclopenten-2-one.

As non-limiting examples for saturated and unsaturated esters or lactones which can be reduced into the corresponding alcohols by silanes according to the invention, there can be cited acetates, propionates, butyrates, isobutyrates, benzoates, acrylates and crotonates, cinnamates, cis-3-hexenoates, sorbates, salicylates, 10-undecylenates, oleates, linoleates, any ester of natural fatty acids and mixtures thereof. All the above-cited esters may, for example, be alkyl or aryl esters, preferably methyl esters. Other non-limitative examples include lactones, such as ε-caprolactone, decalactone, dodecalactone, diketene and sclareolide.

A remarkable property of the catalysts according to the invention is that they allow the reduction of natural triglycerides of fatty acids, like those which form the vegetable and animal oils. In the course of the reaction of a mixed triglyceride derived from distinct fatty acids, there can be obtained simultaneously saturated and unsaturated natural alcohols without any modification of the position or of the stereochemistry of the olefinic double bonds. This is of particular value for olefinic bonds showing a cis-configuration.

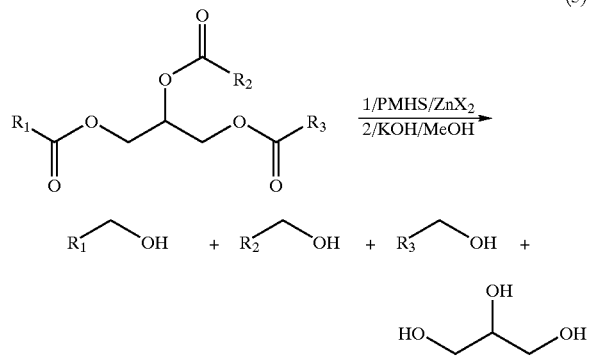

(3)

In the above Scheme (3), the substituents $R_1$, $R_2$ and $R_3$ are hydrocarbon groups which can be identical or different and which can contain from 1 to 20 carbon atoms. In the case where these groups contain one or more olefinc groups of a defined stereochemistry (which, in general, will be cis), the corresponding alcohol obtained after reduction according to the invention will have the same stereochemistry. Thus, oils rich in linoleic and/or linolenic acid, like linseed oil, will be transformed into mixtures rich in linoleyl and/or linolenyl alcohol. Conventional hydrogenation of these vegetable oils is generally carried out at high pressures and temperatures, in contrast with the present invention. Furthermore, because there are used in these conventional hydrogenations the methyl esters of the respective acids obtained by transesterification of the oils with methanol, there is in most cases observed a modification of the stereo-chemistry of the precursor fatty esters in the course of the transesterification and the hydrogenation reaction.

Amongst the triglycerides which can be reduced by the process according to the invention, there can be cited, as non-limiting examples, trioleine, peanut oil, soya oil, olive oil, colza oil, sesame oil, grape-seed oil, linseed oil, cacao butter, palm oil, palm-kernel oil, cotton oil, copra oil, coconut oil, and pork, beef, mutton and chicken fat.

Other oils and fats which are found in nature and which are not triglycerides, but esters of unsaturated fatty acids and monovalent unsaturated alcohols, like jojoba oil and sperm oil, can also be reduced according to the present invention, without any modification of the position or of the stereochemistry of the double bonds present in the ester molecule.

The reaction temperature can vary within a wide range of values, and will in general be in the range of from −50° C. to 250° C. The temperature chosen will depend on the reactivity of the substrate and can be adjusted accordingly without difficulty. More generally, the reaction will be carried out at a temperature within the range of from 50 to 110° C.

The invention will now be illustrated in greater detail in the following examples in which the temperatures are indicated in degrees centigrade, the yields in mole %, the chemical shift δ of the NMR data in ppm, relative to tetramethylsilane as internal reference, and the abbreviations have the usual meaning in the art.

EMBODIMENTS OF THE INVENTION

EXAMPLE 1

Synthesis of the Complex [Zn(benzoate)$_2$(Me$_2$NCH$_2$CH$_2$OH)$_2$]

The compound was prepared as described below and illustrated in scheme (4)

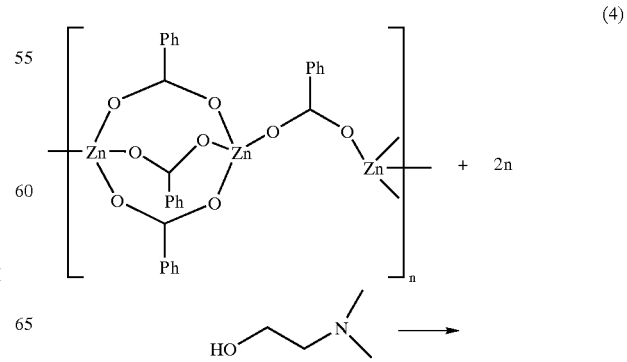

(4)

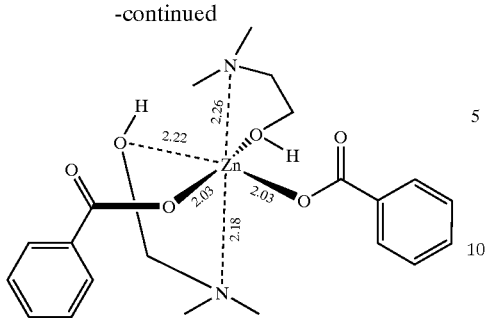

To a suspension of 3.06 g (10 mmol) of zinc benzoate in 50 ml of dichloromethane there were added 1.8 g (20 mmol) of dimethylaminoethanol. An exothermic reaction, followed by complete solution of the zinc benzoate, was observed. After 1 h of stirring at 20° C., the solvent was evaporated, and the solid residue obtained was crystallized from a minimum amount of dichloromethane. There were obtained 3.9 g (80%) of the desired complex as white solid crystals, the structure of which could be obtained by X-ray structure analysis from a single crystal.

NMR($^1$H): $δ_H$: 2.4 (12H, s); 2.65 (2H, t, $CH_2$—N); 3.85 (2H, t, $CH_2$—O); 7.35–7.5 (m, 6H, arom.); 8.1–8.2(d, 4H, arom.);

NMR($^{13}$C): 46.37 (q, $CH_3$); 57.34 (t, $CH_2$—N); 61.02 (t, $CH_2$—O); 127.88 (d); 129.9 (d); 131.19 (d); 135.36 (s); 174.36 (s, $CO_2$—).

EXAMPLE 2
Synthesis of the Complex [Zn(diethylacetate)$_2$(2,2'-bipyridyl)]

This compound was prepared as described, according to scheme (5)

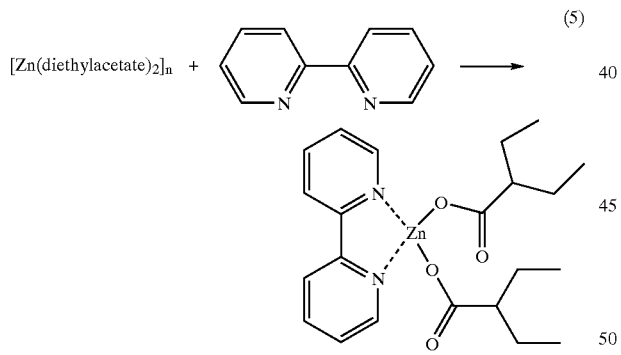

3 g (10 mmole) of zinc diethylacetate were dissolved in 50 ml of diisopropylether. There were then added 10 mmole of the ligand 2,2'-bipyridyl, and the mixture was then stirred at 20° C. A precipitate rapidly formed, which was isolated by filtration and recristallized from cyclohexane. The yield was 80%.

M.p.: 135° C. Analysis: $C_{22}H_{30}N_2O_4Zn$; calculated: C, 58.48; H, 6.69; N, 6.20; found: C, 58.6; H, 6.6; N, 6.15

NMR($^1$H): $δ_H$: 0.85 (12H, t, $CH_3$); 1.45 (4H, m, $CH_2$—); 1.60 (4H, m, $CH_2$—), 2.21 (2H, m, CH=), 7.6 (m, 2H, arom.), 8.05 (m, 2H, arom.), 8.21 (m, 2H, arom.), 9.03 (m, 2H, arom.)

NMR($^{13}$C): 12.13 (q, $CH_3$); 25.75 (t, $CH_2$—), 50.01 (d, CH=); 121.02–149.91 (d,d,d,d,s, arom.); 185.47 (s, $CO_2$—).

EXAMPLE 3
Synthesis of the Complex [Zn(benzoate)$_2$(tetramethylethylenediamine)]

This compound was prepared as described below and outlined in scheme (6)

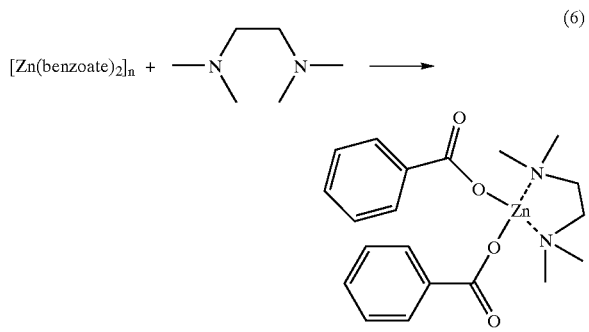

The reaction was carried out as described in example 1, using 1 equivalent of tetramethylethylenediamine instead of the 2 equivalents of dimethylaminoethanol. Yield: 85%.

NMR($^1$H): $δ_H$: 2.62 (12H, s, $CH_3$N); 2.77 (4H, s, $CH_2$—N); 7.3–7.5 (m, 6H, arom.); 8.1 (d, 4H, arom.);

NMR($^{13}$C): 46.57 (q, $CH_3$N); 56.60 (t, $CH_2$—N); 127–131 (d,d,d); 133.8 (s); 175 (s, $CO_2$—).

EXAMPLE 4
Synthesis of the Complexe [Zn(diethylacetate)$_2$(1,2-diaminopropane)$_2$]

This compound was prepared as described below, according to the scheme (7)

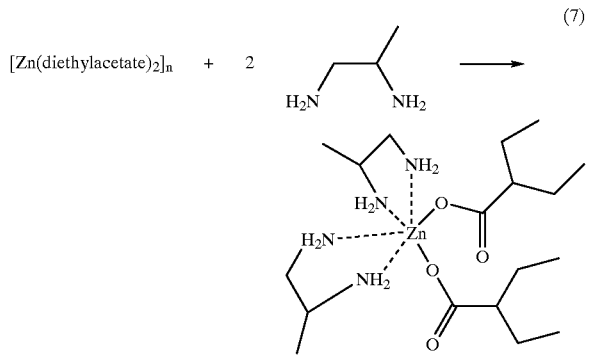

The reaction was carried out as described in example 2, using 2 equivalents of 1,2-diaminopropane instead of 1 equivalent of 2,2'-bipyridyl. Yield=75%.

M.p.: 148° C. Analysis: $C_{18}H_{42}N_4O_4Zn$; calculated: C, 48.70; H, 9.54; N, 12.62; found: C, 48.6; H, 9.6; N, 12.5

NMR($^1$H): $δ_H$: 0.88 (12H, t, $CH_3$); 1.13 (6H, d, $CH_3$); 1.48 (8H, m, $CH_2$—), 2.0 (2H, m, CH=), 2.4 (m, 2H), 2.8–3.5 (m, 12H, $NH_2$), 8.21 (m, 2H, arom.), 9.03 (m, 2H, arom.)

NMR($^{13}$C): 12.57 (q, $CH_3$); 21.44 (q, $CH_3$); 26.05 (t, $CH_2$); 45.73 (t, $CH_2$); 46.61 (d, CH=); 52.27 (d, CH=); 77.29 (d, CH=); 183.30 (s, $CO_2$—).

Reduction Reactions

EXAMPLE 5

Into a three-necked 250 ml flask were charged 30 g of isopropyl ether and 27.2 g of methyl benzoate (0.2 mole), followed by 4 mmole of the crystalline complex prepared according to example 2, e.g. [Zn(diethylacetate)$_2$(2,2'-bipyridyl)]. The mixture was heated to 70° C. (reflux) before adding 30 g of PMHS (0.44 mole) over 15 minutes. The mixture was stirred for one further hour under reflux until complete disappearance of the substrate (monitored by GC analysis). The mixture was then cooled to 20° C. before adding 66 g of an aqueous 45% KOH-solution (0.52 mole) with rapid stirring, followed by further stirring for 1 h. There were then added 100 g of water, and the mixture was decanted. The aqueous phase containing the potassium polymethylsiliconate was decanted, then the organic phase was washed with 50 ml of water. The solvent was removed by distillation, to obtain 21 g of crude product. The distillation from residues gave 20.5 g of benzyl alcohol in a purity greater than 98% (yield=95%).

EXAMPLE 6 (COMPARATIVE)

The reaction was carried out as in example 5, with the exception that 1.12 g (4 mmol) of polymeric zinc diethylacetate were used as catalyst. After 4 h, no reaction of the employed methyl benzoate could be observed, indicating that the presence of an appropriate ligand is essential for the depolymerisation reaction and hence the activation of the zinc diethylacetate for the reduction of the ester.

EXAMPLES 7 TO 23

These examples, summarized in table 1, illustrate the considerable influence that the addition of bidentate ligands has on the catalytic activity of zinc carboxylates in the reduction of methyl benzoate to benzyl alcohol by PMHS. The reaction conditions, resembling those of example 5, are given at the end of the table. This table also gives the position of the infrared bands $\nu(CO_2)_{as}$ and $\nu(CO_2)_s$ of the carboxylate groups of the isolated complexes, which makes it possible to identify the depolymerization of the precursor zinc carboxylate before it attains its catalytic activity.

TABLE 1

Reduction of methyl benzoate to benzyl alcohol. Influence of the nature of the bidentate ligand.

| Example | Zn Carboxylate 2 mole % | Ligand 2 mole % | Infrared $\nu(CO_2)_{as}$ $\nu(CO_2)_s$ cm$^{-1}$ | Yield benzyl alcohol mole % |
|---|---|---|---|---|
| 7 | [Zn(benzoate)$_2$]$_n$ | — | 1639, 1530 1417 | 0 |
| 8 | [Zn(2-Et hexanoate)$_2$]$_n$ | — | 1631, 1554 1417 | 0 |
| 9 | (structure) | — | 1539 1397 | 90 |
| 10 | (structure) | — | 1553 1398 | 85 |
| 11 | [Zn(diethylacetate)$_2$]$_n$ | (Me$_2$N-CH$_2$CH$_2$-OH) (1 eq) | 1595 1421 | 97 |
| 12 | [Zn(diethylacetate)$_2$]$_n$ | (Me$_2$N-CH$_2$CH$_2$-OH) (2 eq) | 1549 1413 | 97 |
| 13 | [Zn(diethylacetate)$_2$]$_n$ | (HO-CH$_2$-CH(NH$_2$)-CH$_2$CH$_3$) | — | 84 |

TABLE 1-continued

Reduction of methyl benzoate to benzyl alcohol. Influence of the nature of the bidentate ligand.

| Example | Zn Carboxylate 2 mole % | Ligand 2 mole % | Infrared $\nu(CO_2)_{as}$ $\nu(CO_2)_s$ cm$^{-1}$ | Yield benzyl alcohol mole % |
|---|---|---|---|---|
| 14 | [Zn(diethylacetate)$_2$]$_n$ | H$_2$N–CH(CH$_3$)–CH$_2$–NH$_2$ | 1555 1407 | 93 |
| 15 | [Zn(diethylacetate)$_2$]$_n$ | Me–NH–CH$_2$CH$_2$–NH–Me | 1605 1400 | 95 |
| 16 | [Zn(diethylacetate)$_2$]$_n$ | Ph–CH(Me)–NH–CH$_2$CH$_2$–HN–CH(Me)–Ph | 1603 1384 | 96 |
| 17 | [Zn(diethylacetate)$_2$]$_n$ | Me$_2$N–CH$_2$CH$_2$–NMe$_2$ | 1564 1422 | 97 |
| 18 | [Zn(2-Et hexanoate)$_2$]$_n$ | Me$_2$N–CH$_2$CH$_2$–NMe$_2$ | — | 98 |
| 19 | [Zn(diethylacetate)$_2$]$_n$ | Me$_2$N–CH$_2$CH$_2$CH(Me)–NMe$_2$ | 1600 1401 | 98 |
| 20 | [Zn(diethylacetate)$_2$]$_n$ | 2,2'-bipyridine | 1606 1420 | 97 |
| 21 | [Zn(diethylacetate)$_2$]$_n$ | pyridine-2-CH=N–CH(Me)Ph | — | 96 |
| 22 | [Zn(diethylacetate)$_2$]$_n$ | Me$_2$N–CH$_2$CH$_2$–NH–Me | 1599 1425 | 97 |
| 23 | [Zn(diethylacetate)$_2$]$_n$ | Me$_2$N–CH$_2$CH$_2$–NH$_2$ | — | 94 |

Reaction conditions:
Methyl benzoate = 20 mmole,
PMHS = 44 mmole,
Zn(carboxylate)$_2$ = 0.4 mmole,
Ligand = 0.4 mmole (if not indicated otherwise).
Solvent = diisopropylether (2 ml), 70° C., 4 h,
Et = ethyl.

EXAMPLES 24 TO 30

These examples, summarized in table 2, illustrate the considerable influence of the addition of monodentate ligands on the catalytic activity of zinc carboxylates in the reduction of methyl benzoate by PMHS. The reactions were carried out as described beforehand, using methyl benzoate as substrate and 2 mole % of zinc diethylacetate together with 4 mole % of the monodentate ligand.

TABLE 2

Reduction of methyl benzoate by PMHS in the presence of zinc carboxylates complexed by monodentate ligands

| Example | Zn Carboxylate 2 mole % | Ligand 4 mole % | Yield PhCH$_2$OH mole % |
|---|---|---|---|
| 24 | [Zn(diethylacetate)$_2$]$_n$ | Triethylamine | 55 |
| 25 | [Zn(diethylacetate)$_2$]$_n$ | Morpholine | 28 |
| 26 | [Zn(diethylacetate)$_2$]$_n$ | Piperidine | 48 |
| 27 | [Zn(diethylacetate)$_2$]$_n$ | 4-tertiobutylpyridine | 88 |
| 28 | [Zn(diethylacetate)$_2$]$_n$ | Hexamethyl-phosphortriamide | 96 |
| 29 | [Zn(diethylacetate)$_2$]$_n$ | Trioctylphosphine oxyde | 38 |
| 30 | [Zn(diethylacetate)$_2$]$_n$ | Dimethylsulfoxyde | 98 |

Reaction conditions:
Methyl benzoate = 20 mmole,
PMHS = 44 mmole,
Zn(carboxylate)$_2$ = 0.4 mmole,
Ligand = 0.8 mmole,
Solvent = diisopropylether (2 ml), 70° C., 4 h,
Et = ethyl.

EXAMPLES 31 TO 36

These examples show that the favorable influence of the addition of the ligands specified beforehand is also existant with respect to the catalytical activity of zinc β-diketonates, like acetylacetonate, for the reduction of esters using PMHS. It is known that zinc acetylacetonate has a trimeric structure which becomes monomeric and octahedric when it is reacted with bidentate ligands, like 2,2'-bipyridine.

Table 3 below shows that zinc acetylacetonate on its own possesses a low activity in the reduction of esters by PMHS.

The addition of 1 equivalent of a primary or secondary diamine to zinc acetylacetonate allows to obtain zinc complexes capable of catalyzing the complete conversion of methyl benzoate to the corresponding alcohol.

TABLE 3

Reduction of methyl benzoate by PMHS in the presence of zinc acetylacetonate complexed by various ligands

| Example | Zinc precursor compound 2 mole % | Ligand 2 mole % | Yield PhCH$_2$OH mole % |
|---|---|---|---|
| 31 | [Zn(acac)$_2$]$_3$ | — | 20 |
| 32 | [Zn(acac)$_2$]$_3$ | 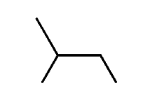 | 98 |
| 33 | [Zn(acac)$_2$]$_3$ | 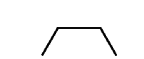 | 97 |
| 34 | [Zn(acac)$_2$]$_3$ | 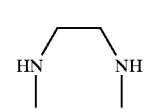 | 95 |
| 35 | [Zn(acac)$_2$]$_3$ |  | 75 |
| 36 | [Zn(acac)$_2$]$_3$ | 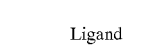 | 53 |

Reaction conditions:
Methyl benzoate = 20 mmole,
PMHS = 44 mmole,
[Zn(acac)$_2$]$_3$ = 0.4 mmole,
Ligand = 0.4 mmole,
acac = acetylacetonate
Solvent = diisopropylether (2 ml), 70° C., 4 h,
Ph = phenyl.

EXAMPLES 37 TO 42

In these examples, there will be shown that the favorable influence of the addition of the ligands specified beforehand is also existant with respect to the catalytical activity of dialkylzinc compounds, like diethylzinc, for the reduction of esters using PMHS (Table 4). Dialkylzinc compounds have a monomeric linear structure with a C—Zn—C angle which is 180° and are unreactive under the conditions of the invention. In the presence of a bidentate ligand L, like a tertiary diamine, they form a monomeric complex of tetrahedral structure ZnR$_2$L [see O'Brien et al., J. Organomet. Chem., 1993, 449, 1 et 1993, 461, 5].

TABLE 4

Reduction of methyl benzoate by PMHS in the presence of diethylzinc complexed by various ligands

| Example | Zinc precursor compound 2 mole % | Ligand 2 mole % | Yield PhCH$_2$OH mole % |
|---|---|---|---|
| 37 | ZnEt$_2$ | — | 0 |
| 38 | ZnEt$_2$ | H$_2$N⌒NH$_2$ | 75 |
| 39 | ZnEt$_2$ | H$_2$N⌒NH$_2$ | 98 |
| 40 | ZnEt$_2$ | HN⌒NH | 94 |
| 41 | ZnEt$_2$ | —N⌒N— | 97 |
| 42 | ZnEt$_2$ | 4-tert-butyl pyridine (4 mole %) | 95 |

Reaction conditions:
Methyl benzoate = 20 mmole,
PMHS = 44 mmole
ZnEt$_2$ = 0.4 mmole,
Ligand = 0.4 mmole (0.8 mmole in Example 42)
Solvent = diisopropylether (2 ml), 70° C. 4 h,
Ph = phenyl,
Et = ethyl.

EXAMPLES 43 TO 47

In these examples, there will be shown that the favorable influence of the addition of the ligands specified beforehand is also existant with respect to the catalytical activity of zinc alcoxydes for the reduction of esters using PMHS. Table 5 shows that the zinc tert-pentoxylate, formed in situ by the addition of 2 equivalents of potassium tert-pentoxyde (in toluene solution) to one equivalent of anhydrous zinc chloride does not shown a pronounced activity for the reduction of methyl benzoate by PMHS, whereas the addition of primary, secondary and tertiary diamines results in highly active catalysts.

TABLE 5

Reduction of methyl benzoate by PMHS in the presence of zinc alcoxydes complexed by various ligands

| Example | Zinc precursor compound 2 mole % | Ligand 2 mole % | Yield PhCH$_2$OH mole % |
|---|---|---|---|
| 43 | Zn(OC$_5$H$_{11}$)$_2$ | — | 51 |
| 44 | Zn(OC$_5$H$_{11}$)$_2$ | H$_2$N–CH(CH$_3$)–CH$_2$–NH$_2$ | 99 |
| 45 | Zn(OC$_5$H$_{11}$)$_2$ | H$_2$N–CH$_2$–CH$_2$–NH$_2$ | 99 |
| 46 | Zn(OC$_5$H$_{11}$)$_2$ | HN(CH$_3$)–CH$_2$–CH$_2$–NH(CH$_3$) | 97 |
| 47 | Zn(OC$_5$H$_{11}$)$_2$ | (CH$_3$)N–CH$_2$–CH$_2$–N(CH$_3$) | 95 |

Reaction conditions:
Methyl benzoate = 20 mmole.
PMHS = 44 mmole,
Zn(OC$_5$H$_{11}$)$_2$ = 0.4 mmole,
Ligand = 0.4 mmole,
Solvent = diisopropylether (2 ml), 70° C., 4 h,
Ph = phenyl.

EXAMPLES 48 TO 52

Reactions were carried out as described in example 5, in refluxing diisopropyl ether, and using a mixture containing 2 mole % of zinc diethylacetate and 2 mole % of dimethylaminoethanol, each with respect to the substrate. There were used 20 mmoles of the respective ester which was reduced with 44 mmoles of PMHS. Hydrolysis was carried out when the substrate had disappeared, using 60 mmoles of KOH (in the form of an aqueous 45% KOH solution). After decantation and evaporation of the solvent, the formed alcohol was distilled. In all cases, the stereochemistry of the starting compound was not affected, as shown by the results presented in Table 6.

TABLE 6

Reduction of different esters by PMHS in the presence of zinc diethylacetate complexed by dimethylaminoethanol

| Example | Substrate | Product | Yield mole % |
|---|---|---|---|
| 48 | cis-CH$_3$CH=CHCH$_2$C(O)OCH$_3$ | cis-CH$_3$CH=CHCH$_2$CH$_2$OH | 95 |
| 49 | geranyl-type ester, CO$_2$Me | corresponding alcohol, CH$_2$OH | 91 |
| 50 | PhCH=CHCO$_2$Me | PhCH=CHCH$_2$OH | 94 |
| 51 | CH$_2$=CH–(CH$_2$)$_8$–CO$_2$Me | CH$_2$=CH–(CH$_2$)$_8$–CH$_2$OH | 97 |

TABLE 6-continued

Reduction of different esters by PMHS in the presence of zinc diethylacetate complexed by dimethylaminoethanol

| Example | Substrate | Product | Yield mole % |
|---|---|---|---|
| 52 | [lactone structure] | [diol structure] | 94 |

Reaction conditions:
Ester = 20 mmole,
PMHS = 44 mmole.
Zn(diethylacetate)$_2$ = 0.4 mmole.
Dimethylaminoethanol = 0.4 mmole.
Solvent = diisopropylether (2 ml), 70° C., 4 h.

EXAMPLES 53 TO 59

Reactions were carried out as described in example 5, in refluxing diisopropyl ether, and using a mixture containing 2 mole % of zinc diethylacetate and 2 mole % of one of the ligands mentioned in Table 7 below, each with respect to the substrate. As substrates, there were used 20 mmoles of the respective aldehyde or ketone, which was reduced with 22 mmoles of PMHS. Hydrolysis was carried out after the substrate had completely disappeared, using 60 mmoles of KOH (in the form of an aqueous 45% KOH solution). After decantation and evaporation of the solvent, the alcohol formed was distilled. The results in Table 7 show that, in all cases, the reduction of aldehydes and ketones proceeded with excellent yields, without any modification of the stereochemistry of the starting compound.

TABLE 7

Reduction of different aldehydes and ketones by PMHS in the presence of zinc diethylacetate complexed by various ligands

| Example | Ligand | Substrate | Product | Yield |
|---|---|---|---|---|
| 53 | Me$_2$N-CH$_2$CH$_2$-NMe$_2$ | [geranial] | [geraniol] | 95 |
| 54 | H$_2$N-CH$_2$CH$_2$-NH$_2$ (N-methyl) | [aldehyde substrate] | [alcohol product] | 88 |
| 55 | Me$_2$N-CH$_2$CH$_2$-NMe$_2$ | [cyclohexene aldehyde] | [cyclohexene alcohol] | 93 |
| 56 | Me$_2$N-CH$_2$CH$_2$-NMe$_2$ | [cyclohexenone] | [cyclohexenol] | 95 |
| 57 | H$_2$N-CH$_2$CH$_2$-NH$_2$ (N-methyl) | [dienone] | [dienol] | 94 |

TABLE 7-continued

Reduction of different aldehydes and ketones by PMHS in the presence of zinc diethylacetate complexed by various ligands

| Example | Ligand | Substrate | Product | Yield |
|---|---|---|---|---|
| 58 | 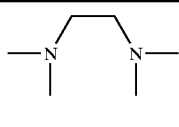 | 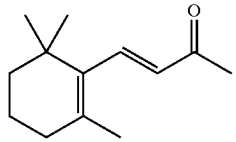 | 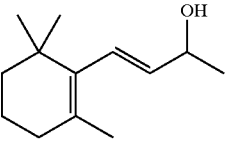 | 90 |
| 59 | 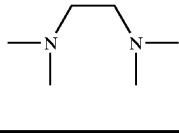 | 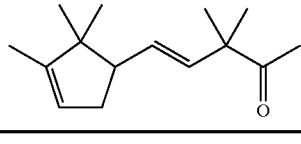 | 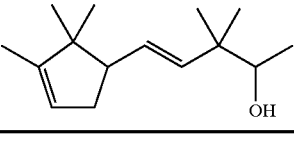 | 95 |

Reaction conditions:
Substrate = 20 mmole,
PMHS = 22 mmole,
Zn(diethylacetate)$_2$ = 0.4 mmole,
Ligand = 0.4 mmole,
Solvent = diisopropylether (2 ml), 70° C. 4 h.

EXAMPLES 60 TO 62

The reactions were carried out as indicated in example 5 and using ZnF$_2$ as catalyst. The results show that zinc halides are active in this type of reduction.

TABLE 8

Reduction of methyl benzoate by PMHS in the presence of ZnF$_2$ complexed by various ligands

| Example | Zinc precursor compound 2 mole % | Ligand 2 mole % | Yield PhCH$_2$OH mole % |
|---|---|---|---|
| 60 | ZnF$_2$ | — | 0 |
| 61 | ZnF$_2$ | 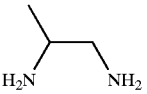 | 97 |
| 62 | ZnF$_2$ | 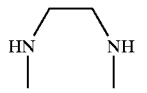 | 93 |

Reaction conditions:
Methyl benzoate = 20 mmole,
PMHS = 44 mmole,
ZnX$_2$ = 0.4 mmole,
Ligand = 0.4 mmole,
Solvent = diisopropylether (2 ml), 70° C., 4 h.

EXAMPLE 63
Reduction of Peanut Oil

A three-necked 1 l flask was charged with 200 ml of toluene, 11 g of zinc 2-ethylhexanoate (0.03 mol) and 5.34 g (0.06 mol) of dimethylaminoethanol. There were then added 200 g of peanut oil and the mixture was heated to reflux (110° C.). 200 g (0.5 mol) of PMHS were added over 1 h, and the mixture was kept under reflux for another 2 h. After this time, GC analysis carried out on samples hydrolyzed by a 30% methanolic KOH solution showed that the amount of alcohol in the reaction mixture was constant. The mixture was then poured into 450 g of a 30% methanolic KOH solution and then kept for 1 further hour at 50° C. There were then added 300 g of water and the mixture decanted. The solvent was then evaporated from the organic phase and the residue distilled at 200–250° C./1 hPa to obtain 100 g of a mixture containing 14% of 1-hexadecanol, 55% of oleyl alcohol and 17% of linoleyl alcohol.

EXAMPLE 64
Reduction of Ethyl Sorbate

A 1 l three-necked flask equipped with a reflux condenser, inner thermometer, syringe pump and magnetical stirrer, was charged with 13.3 g (4 mole % relative to the substrate) of Zn(2-ethylhexanoate)$_2$, 4 g (4 mole %) of dimethylaminoethanol, 10 ml of toluene and heated to 80°. There were then added 210.1 g (1.5 mole) of ethyl sorbate, 0.42 g of BHT (2,4-di-tert-butyl-p-cresol), toluene (ca 200 ml) and the solution was brought to reflux. 213 g (corresponding to 2.1 equivalents) of PMHS were then added over 90 min, and the reaction mixture was then heated to reflux for another 30 min. The mixture was poured on 630 g of a 30% aqueous NaOH-solution until complete hydrolysis, before decanting the organic phase and washing with water. The crude product was distilled on a Vigreux type column (10 h Pa) to obtain 120.7 g (83.4%) of hexa-2,4-dien-1-ol.

EXAMPLE 65
Reduction of Jojoba Oil

A 250 ml three-necked flask equipped with a reflux condenser, inner thermometer, syringe pump and magnetical stirrer, was charged with 50 g of jojoba oil, 0.2 g of Zn(2-ethylhexanoate)$_2$ (corresponding to about 4 mole % per ester function), 0.06 g of dimethylaminoethanol (about 4 mole %) and 50 ml of toluene. The mixture was heated to reflux and 6.5 g (0.1 mole, about 2.2 equivalents) of PMHS were added over 45 min. Reflux was continued for another 30 min, and the reaction mixture was poured into 50 g of a 30% aqueous NaOH solution. After complete hydrolysis, the organic phase was decanted and washed with water. The thus obtained crude product was distilled in a bulb-to-bulb apparatus at 250°/1 h Pa, to obtain 48.4 g (95%) of a product containing 6.4% of (Z)-9-octadecen-1-ol, 59.3% of (Z)-9-icosen-1-ol, 26.8% of (Z)-9-docosen-1-ol and 3.9% of (Z)-9-tetracosen-1-ol.

What is claimed is:

1. A catalyst consisting of a non-hydrido monomeric zinc compound, which is the reaction product of
   i) a precursor zinc compound of formula $ZnX_2$, in which X is an anion selected from the group consisting of carboxylates, β-diketonates, enolates, amides, silylamides, alkyl, cycloalkyl, alkoxy, aryl, aryloxy, alkoxyalkyl, alkoxyaryl, aralkoxy, aralcoyl and alkylaryl groups having from 1 to 20 carbon atoms, halides, carbonates and cyanides; and
   ii) a complexing agent.

2. The catalyst according to claim 1, wherein X is selected from the group consisting of acetate, propionate, butyrate, isobutyrate, isovalerianate, diethylacetate, benzoate, 2-ethylhexanoate, stearate, methoxide, ethoxide, isopropoxide, tert-butoxide, tert-pentoxide, 8-hydroxyquinolinate, naphthenate, substituted and unsubstituted acetylacetonate, tropolonate, a methyl group, an ethyl group, a propyl group, a butyl group and an aryl group.

3. The catalyst according to claim 1, wherein the complexing agent is selected from the group consisting of amines, polyamines, imines, polyimines, aminoalcohols, amine oxides, phosphoramides and amides.

4. The catalyst according to claim 3, wherein the complexing agent is selected from the group consisting of ethylenediamine, N,N'-dimethylethylenediamine, tetramethylethylenediamine, ethanolamine, diethanolamine, dimethylaminoethanol, dimethylformamide, dimethylacetamide, hexamethylphosphortriamide, dimethyl-sulfoxide or 4-tert-butylpyridine.

5. The catalyst according to claim 1, wherein the catalyst has the general formula $ZnX_2L_n$, wherein X is an anion selected from the group consisting of carboxylates, β-diketonates, enolates, amides, silylamides, alkyl, cycloalkyl, alkoxy, aryl, aryloxy, alkoxyalkyl, alkoxyaryl, aralkoxy, aralcoyl and alkylaryl groups having from 1 to 20 carbon atoms, halides, carbonates and cyanides, L is a complexing agent selected from the group consisting of amines, polyamines, imines, polyimines, aminoalcohols, amine oxides, phosphoramides and amides, wherein the anion X and the ligand L can be identical or different, and wherein the ligand and Zn are present in a ratio ranging from 1 to 6.

6. A monomeric carboxylate of zinc, provided that a complex of formula $[Zn(O_2CCH_3)_2(py)_2]$ is excluded.

7. As the carboxylate of claim 6, a complexes of formula
   a) $[Zn(benzoate)_2(dimethylaminoethanol)_2]$,
   b) $[Zn(benzoate)_2(tetramethylethylenediamine)]$,
   c) $[Zn(diethylacetate)_2(1,2-diaminopropane)_2]$, or
   d) $[Zn(diethylacetate)_2(2,2'-bipyridyl)]$.

* * * * *